(12) United States Patent
Hua et al.

(10) Patent No.: US 10,316,310 B2
(45) Date of Patent: Jun. 11, 2019

(54) POLYPEPTIDE HAVING PROTEASE ACTIVITY AND METHODS FOR INCREASING ITS ACTIVITY THEREOF

(71) Applicant: Zhejiang University, Hangzhou, Zhejiang Province (CN)

(72) Inventors: Yuejin Hua, Hangzhou (CN); Yunguang Wang, Hangzhou (CN); Liangyan Wang, Hangzhou (CN)

(73) Assignee: Zhejiang University, Hangzhou, Zhejiang Province (CN)

( * ) Notice: Subject to any disclaimer, the term of this patent is extended or adjusted under 35 U.S.C. 154(b) by 97 days.

(21) Appl. No.: 15/378,035

(22) Filed: Dec. 13, 2016

(65) Prior Publication Data

US 2017/0096652 A1    Apr. 6, 2017

Related U.S. Application Data

(63) Continuation-in-part of application No. PCT/CN2014/079894, filed on Jun. 13, 2014.

(51) Int. Cl.
*C12N 9/52* (2006.01)
*G10H 1/055* (2006.01)
*G10H 1/18* (2006.01)
*G10H 1/00* (2006.01)

(52) U.S. Cl.
CPC ............... *C12N 9/52* (2013.01); *C12Y 304/00* (2013.01); *G10H 1/0066* (2013.01); *G10H 1/0551* (2013.01); *G10H 1/18* (2013.01); *G10H 2220/096* (2013.01); *G10H 2220/121* (2013.01); *G10H 2220/241* (2013.01); *G10H 2220/275* (2013.01); *G10H 2220/461* (2013.01)

(58) Field of Classification Search
CPC combination set(s) only.
See application file for complete search history.

(56) References Cited

FOREIGN PATENT DOCUMENTS

| CN | 101492651 A | 7/2009 |
| CN | 104212782 A | 12/2014 |

OTHER PUBLICATIONS

State Intellectual Property Office of the People's Republic of China (ISR/CN), International Search Report for PCT/CN2014/079894, China, dated Dec. 17, 2015.
State Intellectual Property Office of the People's Republic of China (ISA/CN), Written Opinion of the International Search Authority for PCT/CN2014/079894, China, dated Jan. 28, 2015.
Vujicic-Zagar, A. et al., Crystal Structure of the IrrE Protein, a Central Regulator of DNA Damage Repair in Deinococcaceae, J. Mol. Biol., Dec. 31, 2009, vol. 386, pp. 704-716.

*Primary Examiner* — Kagnew H Gebreyesus
(74) *Attorney, Agent, or Firm* — Shuang Chang; PSK Intellectual Property Group, LLC

(57) ABSTRACT

The present invention relates to a polypeptide having protease activity comprising a zinc finger protease domain, a helix-turn-helix domain and a GAF domain. The core protein sequence of the protease is shown as SEQ ID NO: 1. The invention also relates to optimized reaction conditions for the protease and methods of increasing the protease activity.

6 Claims, 5 Drawing Sheets

Specification includes a Sequence Listing.

SEQUENCE LISTING

<160> NUMBER OF SEQ ID NOS: 8

<210> SEQ ID NO 1
<211> LENGTH: 161
<212> TYPE: PRT
<213> ORGANISM: Deinococcus radiodurans

<400> SEQUENCE: 1

```
Met Pro Ser Ala Asn Val Ser Pro Pro Cys Pro Ser Gly Val Arg Gly
1               5                   10                  15

Gly Gly Met Gly Pro Lys Ala Lys Ala Glu Ala Ser Lys Pro His Pro
            20                  25                  30

Gln Ile Pro Val Lys Leu Pro Phe Val Thr Ala Pro Asp Ala Leu Ala
        35                  40                  45

Ala Ala Lys Ala Arg Met Arg Asp Leu Ala Ala Tyr Val Ala Ala
    50                  55                  60

Leu Pro Gly Arg Asp Thr His Ser Leu Met Ala Gly Val Pro Gly Val
65                  70                  75                  80

Asp Leu Lys Phe Met Pro Leu Gly Trp Arg Asp Gly Ala Phe Asp Pro
                85                  90                  95

Glu His Asn Val Ile Leu Ile Asn Ser Ala Ala Arg Pro Glu Arg Gln
            100                 105                 110

Arg Phe Thr Leu Ala His Glu Ile Gly His Ala Ile Leu Leu Gly Asp
        115                 120                 125

Asp Asp Leu Leu Ser Asp Ile His Asp Ala Tyr Glu Gly Arg Leu
    130                 135                 140

Glu Gln Val Ile Glu Thr Leu Cys Asn Val Ala Ala Ala Ile Leu
145                 150                 155                 160

Met
```

-continued

```
<210> SEQ ID NO 2
<211> LENGTH: 6
<212> TYPE: PRT
<213> ORGANISM: Artificial Sequence
<220> FEATURE:
<223> OTHER INFORMATION: protease cleavage site
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

Glu Leu Xaa Gly Xaa Arg
1               5

<210> SEQ ID NO 3
<211> LENGTH: 6
<212> TYPE: PRT
<213> ORGANISM: Artificial Sequence
<220> FEATURE:
<223> OTHER INFORMATION: protease cleavage site

<400> SEQUENCE: 3

Glu Leu Arg Gly Lys Arg
1               5

<210> SEQ ID NO 4
<211> LENGTH: 6
<212> TYPE: PRT
<213> ORGANISM: Artificial Sequence
<220> FEATURE:
<223> OTHER INFORMATION: protease cleavage site

<400> SEQUENCE: 4

Glu Leu Arg Gly Ala Arg
1               5

<210> SEQ ID NO 5
<211> LENGTH: 6
<212> TYPE: PRT
<213> ORGANISM: Artificial Sequence
<220> FEATURE:
<223> OTHER INFORMATION: protease cleavage site

<400> SEQUENCE: 5

Glu Leu Arg Gly Glu Arg
1               5

<210> SEQ ID NO 6
<211> LENGTH: 6
<212> TYPE: PRT
<213> ORGANISM: Artificial Sequence
<220> FEATURE:
<223> OTHER INFORMATION: protease cleavage site

<400> SEQUENCE: 6

Glu Leu Ala Gly Lys Arg
1               5

<210> SEQ ID NO 7
<211> LENGTH: 6
<212> TYPE: PRT
<213> ORGANISM: Artificial Sequence
<220> FEATURE:
<223> OTHER INFORMATION: protease cleavage site
```

```
<400> SEQUENCE: 7

Glu Leu Ala Gly Ala Arg
1               5

<210> SEQ ID NO 8
<211> LENGTH: 6
<212> TYPE: PRT
<213> ORGANISM: Artificial Sequence
<220> FEATURE:
<223> OTHER INFORMATION: protease cleavage site

<400> SEQUENCE: 8

Glu Leu Ala Gly Glu Arg
1               5
```

POLYPEPTIDE HAVING PROTEASE ACTIVITY AND METHODS FOR INCREASING ITS ACTIVITY THEREOF

CROSS-REFERENCE TO RELATED APPLICATIONS

This application is a continuation-in-part application of International Patent Application No. PCT/CN2014/079894, filed Jun. 13, 2014, which is incorporated herein by reference in its entirety.

FIELD OF THE INVENTION

This invention relates to a polypeptide having protease activity and a method for increasing the activity of the protease.

BACKGROUND OF THE INVENTION

Polypeptide having protease activity, or protease, is a type of enzyme that hydrolyses peptide bonds in proteins. Protease is widely existed in animals, plants and microorganisms.

To date, more than one hundred of commercial proteases are on the market. Due to limited resources of using animals and plants, industrial protease production is mainly from extraction and preparation from *bacillus subtilis*, yeast, mold, *Escherichia coli* and other microorganisms. With in-depth researches on protease, industrial application of proteases has attracted more and more attention. At present, protease has been widely applied in fur, leather, silk, medicine, food, brewing, oil drilling and other industrial fields. The use of proteases for hair-removal and softening in leather industry saves time and improves labor health conditions. Furthermore, protease can also be used for silk degumming, meat tendering, and wine clarification. Clinically, proteases are helpful for treatments of indigestion bronchitis, vasculitis and other symptoms for animals and humans. Moreover, detergents added with proteases can efficiently remove blood and protein on dirty clothes. In addition, proteases are widely used in biochemical and molecular research experiments as a scalpel for proteins, which is indispensable to life science research.

*Deinococcus radiodurans* is an extremophilic bacterium, and is famous for its extremely strong resistance to ionizing radiation, ultraviolet ray, drying, and oxidative stress. Its extreme resistance is partly due to the gene pprI (gene name: dr_0167; GeneID: 1798483), a global regulator for DNA damage response and repair pathways. The gene product PprI (NCBI-GI: 15805204) is composed of 328 amino acids and is comprised of three functional domains: a zinc peptidase-like domain, a helix-turn-helix domain, and a GAF domain. The PprI protein possesses high specificity, strong heat resistance and elevated digestion efficiency, provides an ideal tool for basic scientific research and industrial application. Hence, the use of PprI as protease and the method for increasing its protease activity are especially desirable.

SUMMARY OF THE INVENTION

The present invention relates to a polypeptide having protease activity and methods for increasing the activity of the protease.

The protease possesses three structure domains: a zinc peptidase-like domain, a helix-turn-helix motif and a GAF-like domain. Both the protease and the independent zinc peptidase-like domain alone exhibit the same proteolytic activity. The core protein sequence of the described zinc peptidase-like domain is shown in SEQ ID NO: 1.

```
SEQ ID NO: 1:
MPSANVSPPCPSGVRGGGMGPKAKAEASKPHPQIPVKLPFVTAPDALA
AAKARMRDLAAAYVAALPGRDTHSLMAGVPGVDLKFMPLGWRDGAFDP
EHNVILINSAARPERQRFTLAHEIGHAILLGDDDLLSDIHDAYEGERL
EQVIETLCNVAAAILM
```

The present invention further relates to a use of PprI as protease, with a specific cleavage recognition sequence. The specific cleavage recognition sequence of the present invention is shown in SEQ ID NO: 2: ELXGXR (X represents any kind of essential amino acids). The cleavage site is between the second and the third amino acid residues.

```
SEQ ID NO: 2:            ELXGXR
```

The present invention further relates to the use of PprI as protease and its substrates. One of the substrates of the present protease is the transcription factor DdrO (Gene ID: 1798752; NP_296294.1) in *Deinococcus radiodurans* (ATCC No. 13939). The transcription factor binds to the promoter regions of the DNA damage response gene in vivo or in vitro, and all these promoter regions contain a predicted radiation and desiccation resistance motif (RDRM).

The present invention further relates to a method of increasing the protease activity by carrying out the protease reaction in a proteolytic reaction buffer. The proteolytic reaction buffer is ranged with 100-200 mM NaCl, 10-50 mM Tris-HCl 8.0, 1 mM DTT, and 2.0-5.0 mM $MnCl_2$.

The present invention further relates to a method of increasing the protease activity by carrying out the protease reaction with a temperature range from 4° C. to 65° C., with a preferred temperature range from 35° C. to 40° C.

The present invention further relates to a method of increasing the protease activity by carrying out the protease reaction through binding of the DdrO transcription factor to the described gene promoter regions, including dr0070, dr0099, dra0151, dr0219, dr0326, dra0346, dr0423, dr0596, dr0906, dr1039, dr1143, dr1289, dr1696, dr1771, dr1775, dr1913, dr1921, dr2256, dr2275, dr2336, and dr2574.

The present invention further relates to a method of increasing the protease activity, where the binding reaction between the DdrO transcription factor and the promoter regions is carried out in the buffer containing 100-200 mM NaCl, 20-50 mM Tris-HCl 8.0, 5-10 mM $MgCl_2$ at 30° C.

The present invention further relates to a method of increasing the protease activity, where the minimum sequence for the DdrO transcription factor to bind to the promoter region of the DNA damage response and repair gene is the RDRM site.

The present invention relates to a protease exists in *Deinococcus radiodurans*.

DETAILED DESCRIPTION OF THE INVENTION

The present invention is further illustrated with the following specific examples, but the present invention includes but is not limited to the following steps and contents.

The strains used in the invention are *Deinococcus radiodurans* (ATCC No. 13939), *Escherichia coli* expression strains BL21 (DE3) Chemically Competent Cell (Genetype: F-ompT hsdSB(rB-mB-) gal dcm(DE3), *Escherichia coli* cloning strains Trans5α Chemically Competent Cell (Genetype: F-φ80 lac ZΔM15 Δ(lacZY A-arg F) U169 endA1 recA1 hsdR17(rk-,mk+) supE44λ-thi-1 gyrA96 relA1 phoA).

Embodiment 1

(1). The Proteolytic Activity and Recognition Sequence Specificity of PprI Protease The protease activity of PprI was performed in vitro by incubating its substrate DdrO with PprI for 40 minutes. The final reaction buffer was 150 mM NaCl, 20 mM Tris-HCl pH 8.0, 1 mM DTT, and 2.0 mM $MnCl_2$. The reaction product was detected by SDS-PAGE. DdrO was cleaved by PprI into two fragments. Moreover, through point mutation of the amino acid residues around the DdrO cleavage site, the specific recognition sequences of PprI protease digestion were detected, and they are:

| | |
|---|---|
| SEQ ID NO: 3: | ELRGKR |
| SEQ ID NO: 4: | ELRGAR |
| SEQ ID NO: 5: | ELRGER |
| SEQ ID NO: 6: | ELAGKR |
| SEQ ID NO: 7: | ELAGAR |
| SEQ ID NO: 8: | ELAGER |

In addition, the cleavage site was detected to locate between the second and the third amino acid residues by C-terminal sequencing of the larger cleaved fragment (FIGS. 1-5).

(2). The Optimum Temperature Range and Temperature Resistance of PprI Protease

The optimum temperature range of PprI cleavage activities were between 35° C. and 40° C. When the temperature was between 50° C. and 55° C., the protease activity still existed, but decreased to one third of the optimum activity. The activity was further decreased at 65° C.

Figure 1:
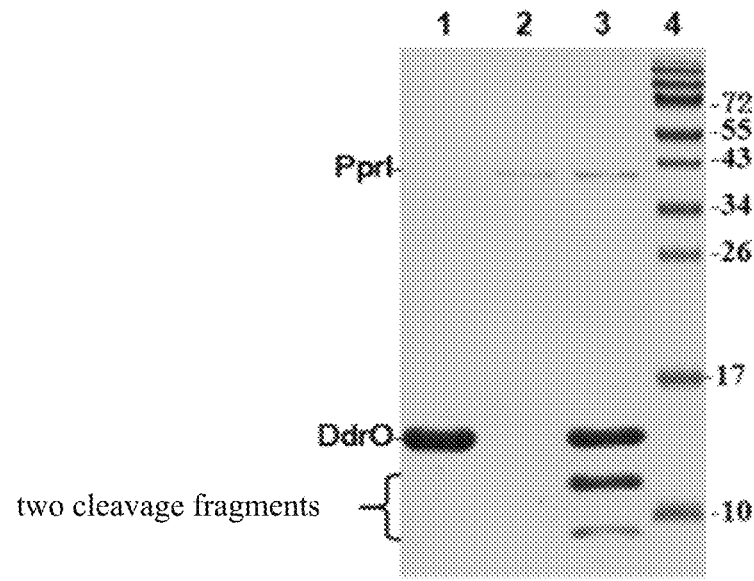
FIG. 1: PprI cleavage activity in vitro detected by SDS-PAGE: Lane 1 shows purified DdrO protein; Lane 2 shows purified PprI protein; Lane 3 shows proteolytic reaction of PprI; Lane 4 shows pre-stained protein marker (Fermentas, SM0671).
Figure 2:
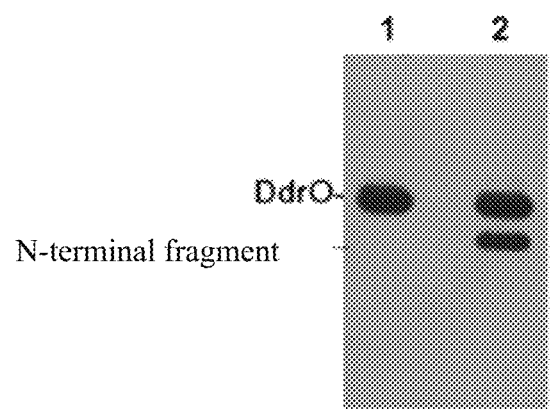
FIG. 2: PprI cleavage activity detected by Western blotting: Lane 1 shows purified DdrO protein; Lane 2 shows proteolytic reaction between PprI and DdrO where PprI cleaves DdrO into two fragments.
Figure 3:
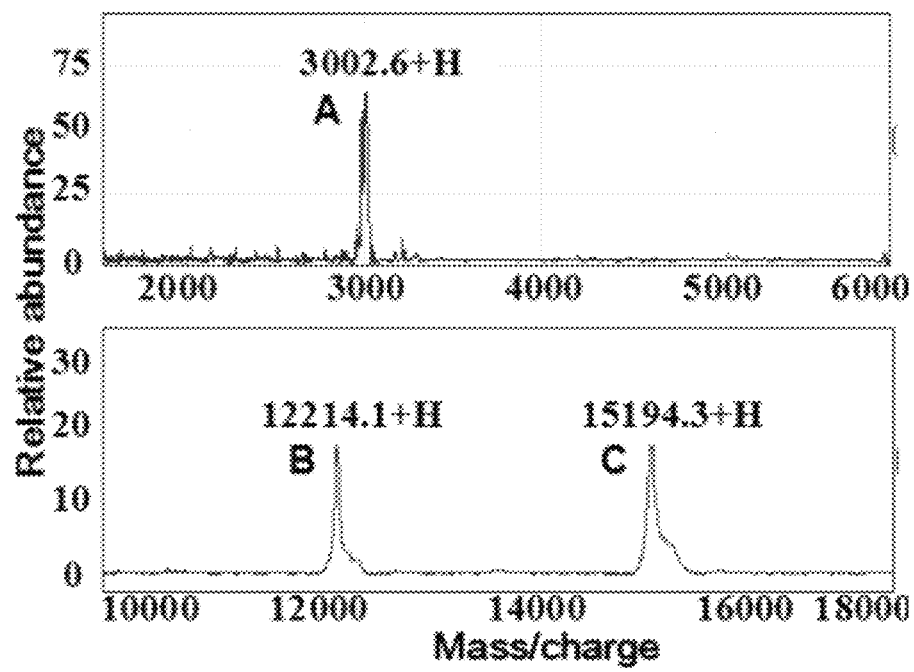
FIG. 3: C-terminal sequencing of the bigger cleaved fragment of DdrO: peak A shows the molecular weight of the smaller fragment; peak B shows the molecular weight of the bigger fragment; peak C shows the molecular weight of the complete substrate DdrO.
Figure 4:
FIG. 4: Alanine scan at the DdrO cleavage site to assay the sequence specificity; WT indicates the wildtype DdrO; Arg-109 and Lys-111 are mutated to Glu.
Figure 5:
FIG. 5: the cleavage model of PprI protease: amino acid residues in bold are essential for recognition and cleavage of the protease. X indicates the variable amino acid residue; the arrow points to the cleavage site.
Figure 6:
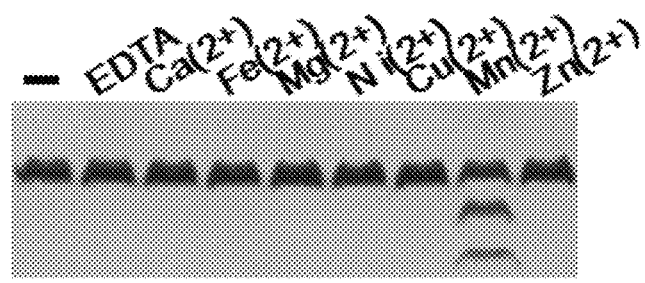
FIG. 6: metal ion scans for the PprI protease activity detected by SDS-PAGE: from left to right: without additive, EDTA, $CaCl_2$, $FeCl_2$, $MgCl_2$, $NiSO_4$, $CuCl_2$, $MnCl_2$, $ZnCl_2$; the concentration of all the metal ions is 1 mM.

(3). Increasing the PprI Cleavage Activity by Optimizing the Manganese Ion Concentration PprI protease activity was increased by the presence of Me and the optimum final concentration of $Mn^{2+}$ was 2 mM (FIG. 6).

Figure 7:
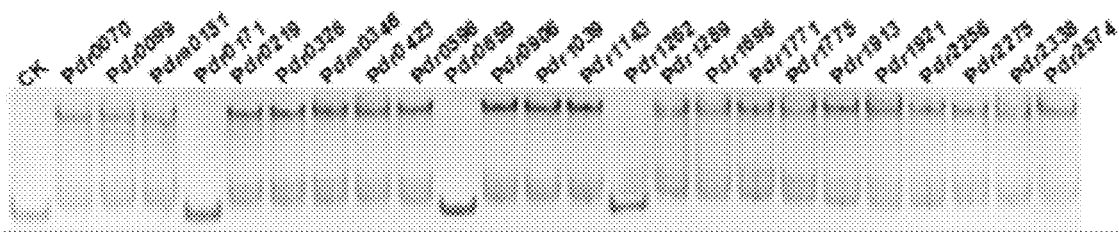
FIG. 7: DdrO binding to the promoter regions containing RDRM in vitro: CK shows a negative control without adding DdrO; the other lanes show the binding of DdrO to the promoter regions of the DDR genes containing RDRM site.

(4). Increasing the PprI Cleavage Activity by Optimizing the DdrO Binding Activities to the Promoter Regions Containing RDRM Site In Vitro The promoter region of dr2340 was added to the binding buffer (200 mM NaCl, 50 mM Tris-HCl 8.0, 10 mM $MgCl_2$) without DdrO for 40 minutes. The product was detected by 12% TB-PAGE. The experiment showed that the DNA band did not shift when DdrO protein was not added (FIG. 7).

Figure 8:
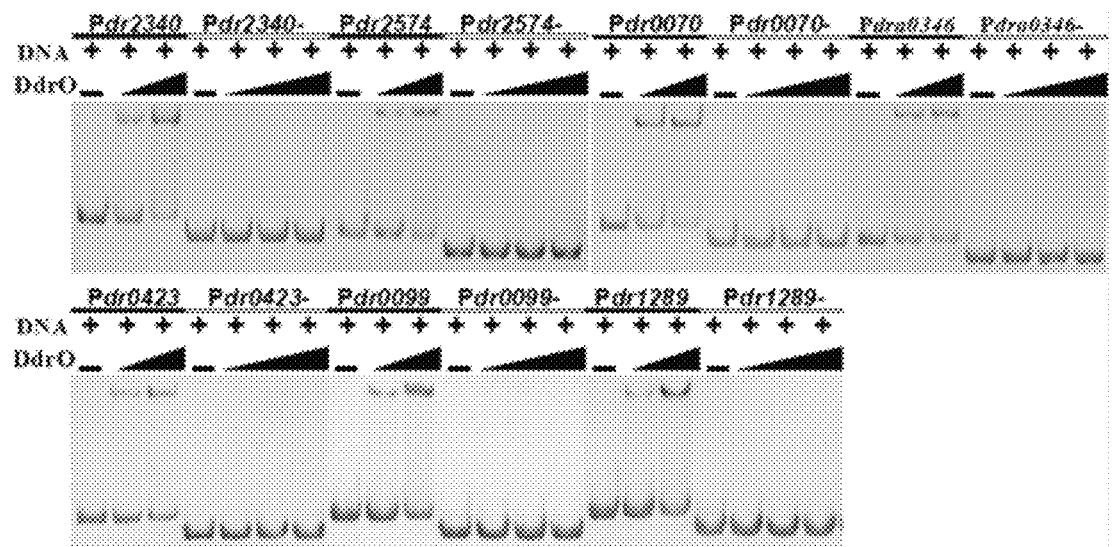
FIG. 8: shows the minimum DdrO binding sequence: seven promoters containing RDRM site were selected; PrecA (i.e. Pdr2340, etc.) shows the complete promoter with RDRM site, PrecA– (i.e. Pdr2340–, etc.) is the truncated promoter without the RDRM site. The promoters containing the RDRM site can be bound by DdrO, the promoters do not contain the RDRM site cannot be bound. The final concentration of DdrO is 0.8-2.4 µM.

(5). The RDRM Site of the Gene Promoter Regions is Essential for Increasing the PprI Cleavage Activity by Optimizing the DdrO Binding Activities In Vitro The promoter regions of dr0326, dra0346 and dr2574 were reacted with the DdrO in the binding buffer (200 mM NaCl, 50 mM Tris-HCl PH 8.0, 10 mM $MgCl_2$) for 40 minutes. The EMSA experiments showed that all the promoter regions could bind to DdrO (FIG. 8).

(6). DdrO Binds to the Promoter Regions Containing RDRM Site In Vivo

Figure 9:
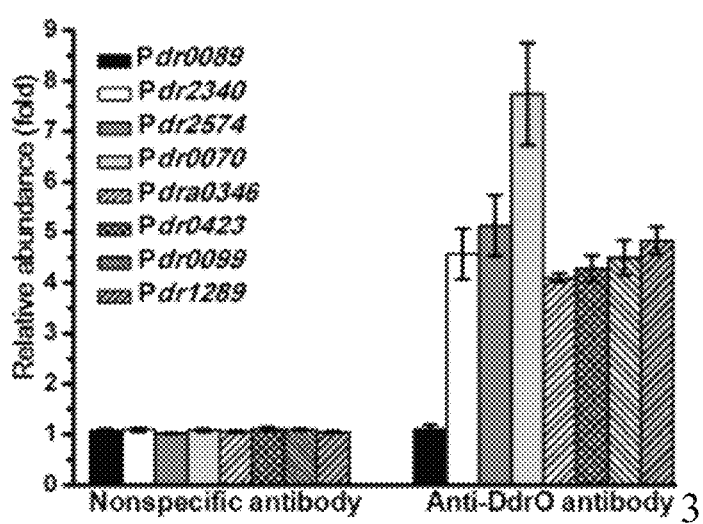
FIG. 9: DdrO binds to the promoter regions of DDR genes in vivo: QRT-PCR was performed using the immunoprecipitated DNA. DNA fragments cross-linked to DdrO were enriched by rabbit anti-DdrO antibody. Nonspecific normal antibody of rabbit in ChIP assay was applied as a blank control. dr0089, a house-keeping gene, was used as a normalization factor.

Chromatin-immunoprecipitation assay was performed. DNA fragments cross-linked to DdrO were enriched by rabbit anti-DdrO antibody. QRT-PCR analysis showed that transcription of dr0070 and dr0099 in wildtype strain R1 was up-regulated significantly after exposure to radiation. Nonspecific normal antibody of rabbit in ChIP assay was applied as a blank control. Dr0089 was used as a normalization factor in qRT-PCR (FIG. 9).

Figure 10:
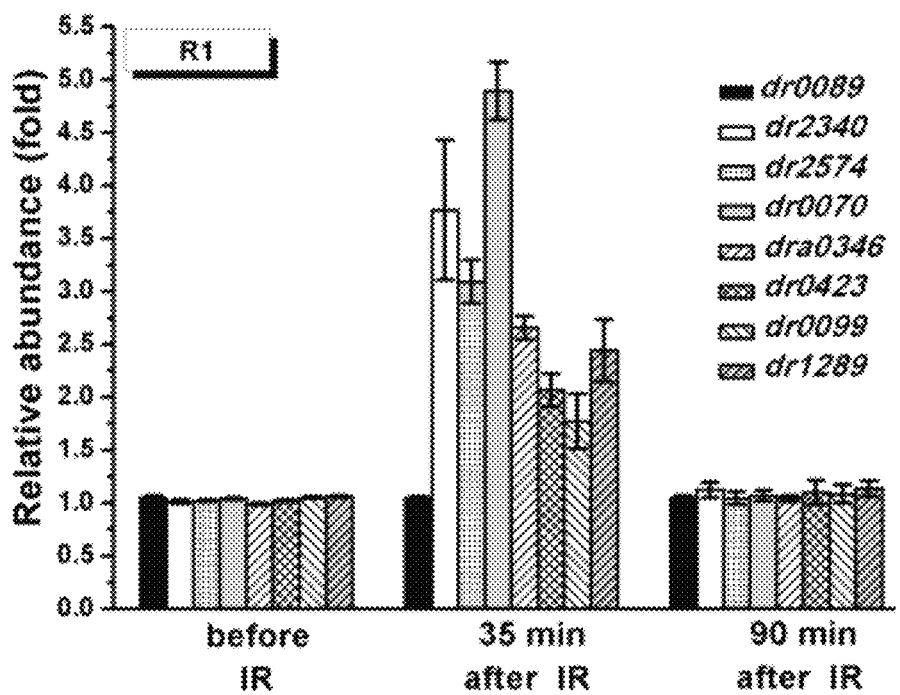
FIG. 10: RNA transcription of the wildtype strain after exposure to gamma radiation. Three time points were chosen: before radiation, recovery for 35 minutes and recovery for 90 minutes after the radiation.
Figure 11:
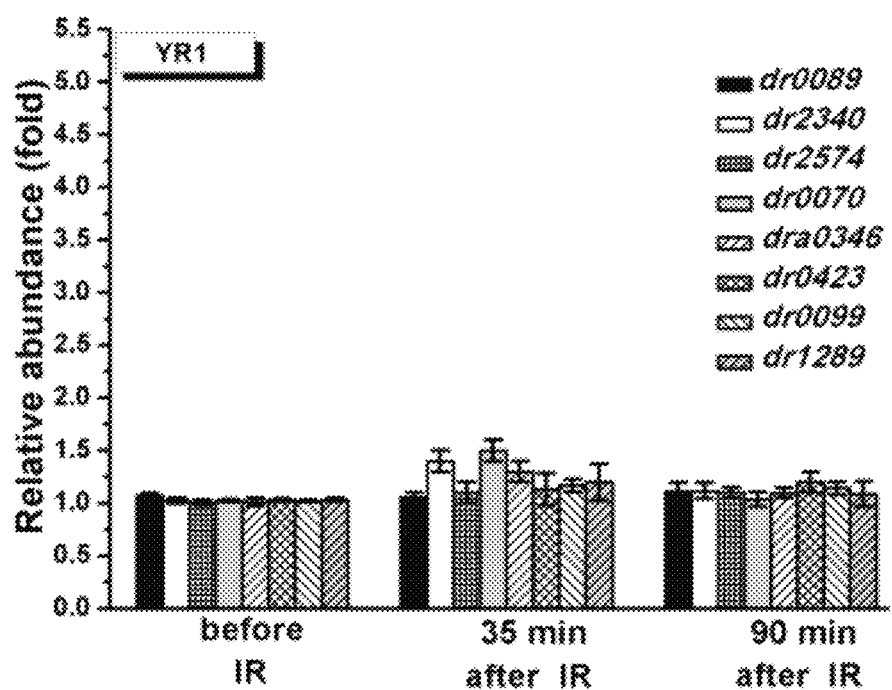
FIG. 11: RNA transcription of the pprI-knockout strain after exposure to gamma radiation. Three time points were chosen: before radiation, recovery for 35 minutes and recovery for 90 minutes after the radiation.

(7). The Transcription Level of DDR Genes in Wildtype Strain R1 and pprI-Knockout Strain YR1 Before Exposure to Radiation Before exposure to radiation, wildtype strain R1 and pprI-knockout strain YR1 were collected, followed by RNA extraction, reverse transcription, and qRT-PCR. The results showed that transcription levels of dr2340, dr2574, dr0070, dra0346, dr0423, dr0090 and dr1289 were unchanged in the mutant YR1 relative to the wildtype R1 before exposure to radiation. dr0089 was used as a normalization factor (FIGS. 10-11).

Embodiment 2

The protease activity of PprI was performed in vitro by incubating its substrate DdrO with PprI for 40 minutes. The final reaction buffer was 100 mM NaCl, 30 mM Tris-HCl pH 8.0, 1 mM DTT, and 3.0 mM $MnCl_2$. The reaction product was detected by SDS-PAGE, and DdrO was cleaved by PprI into two fragments. Moreover, through point mutation of the amino acid residues around the DdrO cleavage site, the specific recognition sequences of PprI protease digestion were detected, and they are:

```
SEQ ID NO: 3:        ELRGKR
SEQ ID NO: 4:        ELRGAR
SEQ ID NO: 6:        ELAGKR
SEQ ID NO: 7:        ELAGAR
```

In addition, the cleavage site was detected to locate between the second and the third amino acid residues by C-terminal sequencing of the larger cleaved fragment (FIGS. 1-5).
(2). The Optimum Temperature Range and Temperature Resistance of PprI Protease The optimum temperature range of PprI cleavage activities were between 35° C. and 40° C. The protease activity remained the highest during this temperature range and was consistent. When the temperature was 4° C., the protease activity still existed, but was weaker. When the temperature was 65° C., the protease activity was also weaker.
(3). Increasing the PprI Cleavage Activity by Optimizing the Manganese Ion Concentration PprI protease activity requires the presence of $Mn^{2+}$ and was increased to the optimum level when the final concentration of $Mn^{2+}$ was 2 mM. When the final concentration of the other metal ions (such as $Ni^{2+}$, $Zn^{2+}$) was higher than 0.25 mM, the cleavage activity was inhibited (FIG. 6).
(4). Increasing the PprI Cleavage Activity by Optimizing the DdrO Binding Activities to the Promoter Regions Containing RDRM Site In Vitro DdrO and the promoter regions of dr0070, dr0099, dra0151, dr0219, dr0326, dra0346, dr0423 dr0596, dr0906 and dr1039, respectively, was added to the binding buffer (200 mM NaCl, 50 mM Tris-HCl 8.0, 5 mM $MgCl_2$) for 40 minutes. The products were detected by 12% TB-PAGE, the experiment showed that the DNA bands shifted when each of the promoters was added to the DdrO protein (FIG. 7).
(5). The RDRM Site of the Gene Promoter Regions is Essential for Increasing the PprI Cleavage Activity by Optimizing the DdrO Binding Activities In Vitro The promoter regions that do not contain the RDRM site, Pdr0070-, Pdr0099-, Pdr2338- and Pdr0423-, were reacted with DdrO in the binding buffer (200 mM NaCl, 50 mM Tris-HCl PH 8.0, 5 mM $MgCl_2$) for 40 minutes. The products were detected by 12% TB-PAGE. The experiment showed that the DNA bands did not shift when each of the promoters was added to the DdrO protein (FIG. 8).
(6). DdrO Binds to the Promoter Regions Containing RDRM Site In Vivo Chromatin-immunoprecipitation assay was performed. DNA fragments cross-linked to DdrO were enriched by rabbit anti-DdrO antibody. The transcriptions of dr0326 and dra0346 were detected by qRT-PCR. The results showed that the quantity of selected promoters enriched by specific anti-DdrO antibody were 3 to 6 fold higher than that enriched by non-specific antibody (FIG. 9).
(7). The Transcription Level of DDR Genes are Up-Regulated in Wild Type Strain R1 Relative to the PprI-Knockout Strain YR1 after Exposure to Radiation After exposure to 2 KGy gamma radiation, wild-type strain R1 and pprI-knockout strain YR1 were recovered in the fresh media for 35 minutes and collected, followed by RNA extraction, reverse transcription, and qRT-PCR. The results showed that the transcription levels of dr2340, dr2574, dr0070, dra0346, dr0423, dr0090 and dr1289 were up-regulated after exposure to gamma radiation in wild-type R1, while the transcription level was unchanged in the pprI mutant YR1. The house-keeping gene, dr0089, was used as a normalization factor (FIGS. 10-11).

Embodiment 3

The protease activity of PprI was performed in vitro by incubating its substrate DdrO with PprI for 40 minutes. The final reaction buffer was 150 mM NaCl, 20 mM Tris-HCl pH 8.0, 1 mM DTT, and 5.0 mM $MnCl_2$. The reaction product was detected by SDS-PAGE, and DdrO was cleaved by PprI into two fragments. Moreover, through point mutation of the amino acid residues around the DdrO cleavage site, the specific recognition sequences of PprI protease digestion were detected, and they are:

```
SEQ ID NO: 3:        ELRGKR
SEQ ID NO: 4:        ELRGAR
SEQ ID NO: 5:        ELRGER
SEQ ID NO: 6:        ELAGKR
SEQ ID NO: 7:        ELAGAR
SEQ ID NO: 8:        ELAGER
```

In addition, the cleavage site was detected to locate between the second and the third amino acid residues by C-terminal sequencing of the larger cleaved fragment (FIGS. 1-5).
(2). The Optimum Temperature Range and Temperature Resistance of PprI Protease The optimum temperature range of PprI cleavage activity was between 35° C. and 40° C. When the temperature was within the range, the protease remained the highest activity. The activity was relatively weaker at 4° C. When the temperature was between 50° C. and 55° C., the protease activity still existed, but decreased to one third of the optimum activity.
(3). Increasing the PprI Cleavage Activity by Optimizing the Manganese Ion Concentration PprI protease activity requires the presence of $Mn^{2+}$. When the final optimum concentration was 5 mM, the activity was still existed. When the final concentration of the other metal ions (such as $Fe^{2+}$, $Cu^{2+}$) was higher than 0.25 mM, the cleavage activity was inhibited (FIG. 6).

(4). Increasing the PprI Cleavage Activity by Optimizing the DdrO Binding Activities to the Promoter Regions Containing RDRM Site In Vitro The promoter region of dr2340 was added to the binding buffer (200 mM NaCl, 50 mM Tris-HCl 8.0, 10 mM $MgCl_2$) without DdrO for 40 minutes. The product was detected by 12% TB-PAGE. The experiment showed that the DNA band did not shift when DdrO protein was not added (FIG. 7).

(5). The RDRM Site of the Gene Promoter Regions is Essential for Increasing the PprI Cleavage Activity by Optimizing the DdrO Binding Activities In Vitro The promoter regions of dr0326, dra0346 and dr2574 were reacted with DdrO in the binding buffer (200 mM NaCl, 50 mM Tris-HCl PH 8.0, 10 mM $MgCl_2$) for 40 minutes, and then detected by 12% TB-PAGE. The EMSA experiments showed that all the promoter regions could bind to DdrO (FIG. 8).

(6). DdrO Binds to the Promoter Regions with RDRM Site In Vivo

Chromatin-immunoprecipitation assay was performed. DNA fragments cross-linked to DdrO were enriched by rabbit anti-DdrO antibody. The transcription of negative control, dr0089 was detected by qRT-PCR. The result showed that the quantity of dr0089 promoter enriched by specific anti-DdrO antibody was consistent with that enriched by non-specific antibody (FIG. 9).

(7). The Transcription Levels of DDR Genes in Wild Type Strain R1 and PprI-Knockout Strain YR1 During the Post-Recovery Period After exposure to 2 KGy gamma radiation, wildtype strain R1 and pprI-knockout strain YR1 were recovered in the fresh media for 90 minutes and collected, followed by RNA extraction, reverse transcription, and qRT-PCR. The results showed that transcription levels of dr2340, dr2574, dr0070, dra0346, dr0423, dr0090 and dr1289 were unchanged in both the wild-type R1 and the pprI mutant YR1 during the post-recovery period. The house-keeping gene, dr0089, was used as a normalization factor (FIGS. 10-11).

Strain used in the above embodiments is *Deinococcus radiodurans* (ATCC No. 13939). Furthermore, according to the teachings and enlightenment of the present invention, any synthetic or other natural protease and derivatives, such as PprI homologous sequence, similar structure and function, is also within the protection scope of the present invention.

Finally, it should be declared that the above examples are merely used to help those skilled in the art to understand the present invention, rather than to limit the protection scope of the present invention, and any relevant technical solutions obtainable by those skilled in the art according to general technical knowledge and common knowledge fall within the protection scope of the present invention.

What is claimed is:

1. A method for producing a composition comprising a polypeptide with increased protease activity where the polypeptide is isolated from *Deinococcus radiodurans*, comprising the following steps of:

Step 1, preparing a proteolytic reaction buffer of 150 mM NaCl, 20 mM Tris-HCl PH 8.0, 1.0 mM DTT, 2.0 mM $MnCl_2$;

Step 2, adding a promoter comprising the DNA damage response gene containing the predicted radiation and desiccation resistance motif (RDRM) and a substrate consisting of transcription factor DdrO (Gene ID: 1798752; NP 296294.11) from *Deinococcus radiodurans* (ATCC No. 139391) to the proteolytic reaction buffer and incubate for a period of time to form a substrate buffer; and Step 3, adding the polypeptide to the substrate buffer and maintain a temperature in a range of 35-40° C., Wherein the polypeptide comprises a zinc peptidase-like domain containing polypeptide fragment of PR 1 (GI: 158052041) consisting of SEQ ID No: 1.

2. The method of claim 1, wherein the specific cleavage recognition sequence of said polypeptide is SEQ ID No: 2 (ELXGXR, where X is any kind of essential amino acids), and the cleavage site is between the second and the third amino acid residue.

3. The method of claim 1, wherein the specific cleavage recognition sequence is one of SEQ ID No: 3-8.

4. The method of claim 1, wherein gene promoter regions containing the RDRM site include dr0070, dr0099, dra0151, dr0219, dr0326, dra0346, dr0423, dr0596, dr0906, dr1039, dr1143, dr1289, dr1696, dr1771, dr1775, dr1913, dr1921, dr2256, dr2275, dr2336, and dr2574.

5. The method of claim 1, wherein the binding reaction between DdrO and the promoter regions containing the RDRM site is carried out in the buffer containing 150 mM NaCl, 20 mM Tris-HCl 8.0, 5 mM MgCl2 at 30° C.

6. The method of claim 1, wherein the minimum sequence for DdrO to bind to the promoter regions of the DNA damage response and repair gene is the RDRM site.

* * * * *